United States Patent
Ijichi et al.

(10) Patent No.: US 6,955,264 B2
(45) Date of Patent: Oct. 18, 2005

(54) METHOD OF DETECTING PROTRUSION OF INSPECTION OBJECT FROM PALETTE AND METHOD OF FABRICATING SEMICONDUCTOR DEVICE

(75) Inventors: Toshiya Ijichi, Hyogo (JP); Shinji Semba, Hyogo (JP)

(73) Assignee: Renesas Technology Corp., Tokyo (JP)

( * ) Notice: Subject to any disclaimer, the term of this patent is extended or adjusted under 35 U.S.C. 154(b) by 213 days.

(21) Appl. No.: 10/145,154

(22) Filed: May 15, 2002

(65) Prior Publication Data

US 2003/0104642 A1 Jun. 5, 2003

(30) Foreign Application Priority Data

Jul. 18, 2001 (JP) .......................................... 2001-217643

(51) Int. Cl.$^7$ ................................................. B07C 5/00
(52) U.S. Cl. ......................... 209/546; 209/583; 209/630
(58) Field of Search ................................. 209/546, 583, 209/630; 712/38; 710/16; 713/407

(56) References Cited

U.S. PATENT DOCUMENTS

| | | | | |
|---|---|---|---|---|
| 5,142,677 A | * | 8/1992 | Ehlig et al. .................. | 718/108 |
| 6,263,419 B1 | * | 7/2001 | Boutaud et al. .............. | 712/38 |
| 6,311,264 B1 | * | 10/2001 | Boutaud et al. .............. | 712/38 |
| 6,610,954 B2 | * | 8/2003 | Takizawa ..................... | 209/583 |
| 6,651,820 B2 | * | 11/2003 | Takizawa ..................... | 209/546 |

FOREIGN PATENT DOCUMENTS

| | | |
|---|---|---|
| JP | 11-106047 | 4/1999 |
| KR | 1997-011869 | 11/1998 |
| KR | 1999-0054408 | 3/2002 |

* cited by examiner

*Primary Examiner*—John F. Niebling
*Assistant Examiner*—Andre' Stevenson
(74) *Attorney, Agent, or Firm*—McDermott, Will & Emery (57) ABSTRACT

In order to provide a method of detecting protrusion of an inspection object from a palette improved to be capable of making highly precise detection and reducing a socket breakage ratio, an inspection object is introduced into each of a plurality of pockets provided on the surface of a palette, which in turn is transported. A reflection level of the inspection object stored in each of the plurality of pockets is measured every palette with a reflection type photoelectric sensor. The maximum value and the minimum value of the reflection level are obtained from data of every palette, for calculating a dispersion width defined by the difference between the maximum value and the minimum value. The dispersion width is compared with a previously set determination threshold, for determining whether or not the dispersion width is greater than the determination threshold.

7 Claims, 9 Drawing Sheets

METHOD OF DETECTING PROTRUSION OF INSPECTION OBJECT FROM PALETTE AND METHOD OF FABRICATING SEMICONDUCTOR DEVICE

BACKGROUND OF THE INVENTION

1. Field of the Invention

The present invention generally relates to a method of detecting protrusion of an inspection object from a palette, and more specifically, it relates to a method of detecting protrusion of an inspection object from a palette improved to be capable of remarkably widening a determination margin and implementing stable detection. The present invention also relates to a method of fabricating a semiconductor device comprising such a method of detecting protrusion of an inspection object from a palette.

2. Description of the Prior Art

A conventional semiconductor tester brings leads of integrated circuits (hereinafter abbreviated as ICs) into contact with electrodes provided in sockets, for testing electric characteristics of the ICs. In order to transport workpieces (ICs) in the semiconductor tester, a magazine containing stacked pallets, dedicated to transportation, storing ICs is set on an in-loader so that the palettes are sliced from the in-loader one by one and horizontally transported to a test part.

The ICs are tested by bringing the leads thereof into contact with the electrodes provided in the sockets. In this method, the ICs stored in each palette are pushed up and brought into contact with the sockets arranged above the palette. The sockets are arranged upward, to be prevented from collecting solder residues. Further, cooling air or hot air is blown to the test part for maintaining the environmental temperature in the test. The test part is provided in an adiabatic vessel, for circulating the air.

Figure 10:
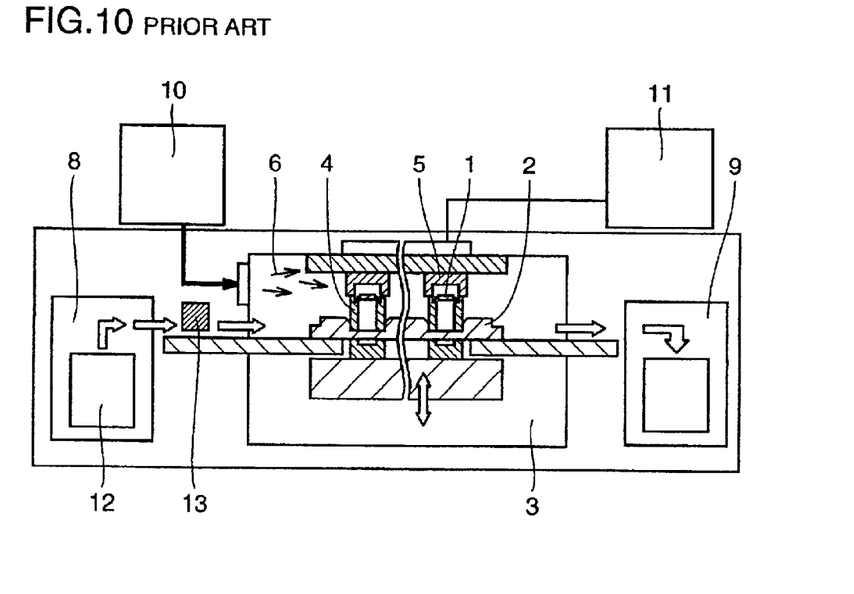
FIG. 10 is a conceptual diagram of a conventional semiconductor tester.

FIG. 10 is a block diagram of a conventional semiconductor tester 11 having the aforementioned test part.

Referring to FIG. 10, ICs 1 are placed on push-up parts 4 for pushing up the ICs 1 toward sockets 5. A transport palette 2 horizontally transports the ICs 1. A cooling air generator 10 introduces cooling air 6 into a test part 3. A magazine 12 is inserted in an in-loader 8, so that the ICs 1 pass through an IC protrusion detection part 13. The ICs 1 tested by the tester 11 are transferred to an out-loader 9.

Figure 11:
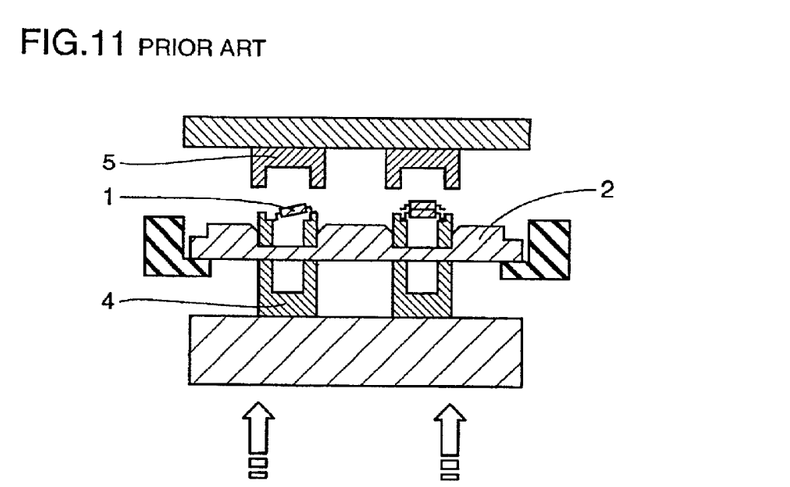
FIG. 11 is a first diagram for illustrating a problem of a conventional method.

In the aforementioned structure of the test part 3, any IC 1 may protrude from a pocket of the transport palette 2 to cause displacement and two ICs 1 may overlap with each other in the same pocket as shown in FIG. 11, to unstabilize contact between the leads of the ICs 1 and socket electrodes and hinder a normal test.

Figure 12:
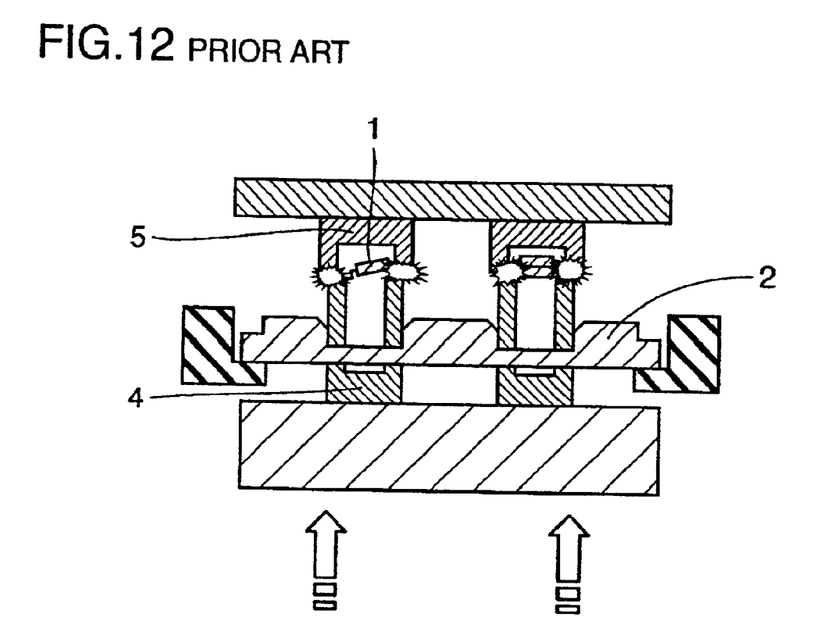
FIG. 12 is a second diagram for illustrating another problem of the conventional method.

In this case, the protruding and overlapping ICs 1 may break the push-up parts 4 and the sockets 5 as shown in FIG. 12, to disadvantageously reduce workability of the overall tester 11 and deteriorate productivity.

Therefore, it is necessary to detect whether or not the ICs 1 are normally stored in the pockets of the transport palette 2 immediately before testing the same in the test part 3.

Figure 13:
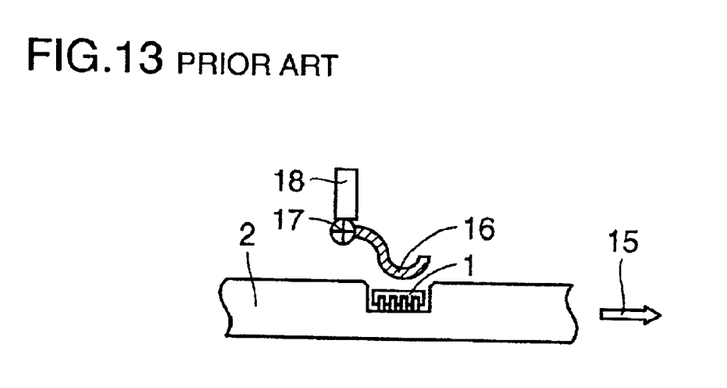
FIG. 13 is a conceptual diagram showing a conventional lever-type detection method.

FIG. 13 shows a conventional detection method employing a lever-type detection mechanism. In this lever-type detection mechanism, the transport palette 2 transports the ICs 1 along arrow 15. A protrusion detection lever 16 is fixed to a limit sensor 18 through a support point 17.

However, this method can detect no IC 1 protruding from the pocket storing the same, and is insufficient in function.

Figure 14:
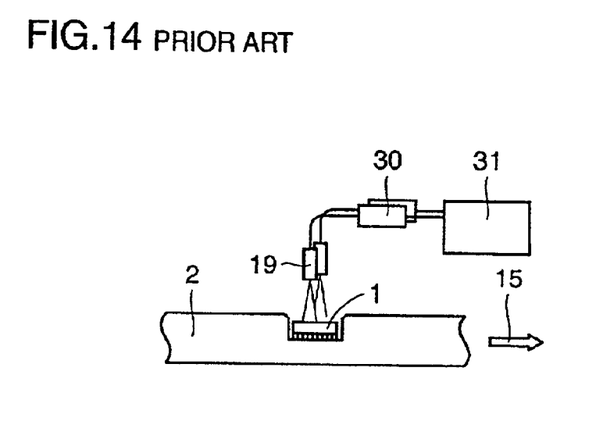
FIG. 14 is a diagram for illustrating a conventional optical sensor-type detection method.

FIG. 14 illustrates another conventional method employing an optical sensor type detection mechanism.

Referring to FIG. 14, the ICs 1 are placed on the transport palette 2 and transported along arrow 15. Reflection type photoelectric sensors 19 are connected to a controller 31 through sensor amplifiers 30. While this method can detect any IC 1 protruding from the pocket storing the same, a threshold for determining defectiveness/non-defectiveness is set between the lower limit for defectives and the upper limit for non-defectives for making detection in units of ICs by comparing absolute values. Therefore, the margin for setting the threshold is disadvantageously reduced while reflection levels on the surfaces of the ICs 1 vary with the types of the ICs 1. The latter problem results from difference between molds varying with the types of the ICs 1 and the degrees of soiling of the molds. Therefore, it is difficult to make stable and precise detection by this method due to remarkable dispersion.

SUMMARY OF THE INVENTION

The present invention has been proposed in order to solve the aforementioned problems, and an object thereof is to provide a method of detecting protrusion of an inspection object from a palette improved to be capable of remarkably widening a determination margin and implementing stable detection.

Another object of the present invention is to provide a method of fabricating a semiconductor device including steps of the aforementioned protrusion detection method.

In the method of detecting protrusion of an inspection object from a palette according to the present invention, an inspection object is first introduced into each of a plurality of pockets provided on the surface of a palette, which in turn is transported. A reflection level of the inspection object stored in each of the aforementioned plurality of pockets is measured every palette with a reflection type photoelectric sensor. The maximum value and the minimum value of the aforementioned reflection level are obtained from data of every palette, for calculating a dispersion width defined by the difference between the maximum value and the minimum value. The aforementioned dispersion width is compared with a previously set determination threshold, for determining whether or not the dispersion width is greater than the determination threshold.

According to a preferred mode of the present invention, the aforementioned inspection object includes an IC.

According to another preferred mode of the present invention, measuring points for the reflection level of the aforementioned inspection object are arranged in two rows along the direction of the aforementioned transportation on the inspection object, for measuring the reflection level of the aforementioned inspection object on two points aligning with each other on one of the aforementioned two rows and two points aligning with each other on the other one of the aforementioned two rows.

According to still another preferred mode of the present invention, the method detects protrusion of the aforementioned inspection object from the corresponding pocket while detecting whether or not the aforementioned inspection object overlaps with another inspection object in the corresponding pocket by the aforementioned determination.

According to a further preferred mode of the present invention, the aforementioned plurality of pockets are arranged in two rows along the direction of transportation on the aforementioned palette.

According to a further preferred mode of the present invention, the distance between the aforementioned inspection object and the aforementioned reflection type photoelectric sensor is set to 1.0 mm to 2.0 mm, for measuring the aforementioned reflection level.

In the method of fabricating a semiconductor device according to another aspect of the present invention, an IC is first introduced into each of a plurality of pockets provided on the surface of a palette, which in turn is transported. A reflection level of the aforementioned IC stored in each of the aforementioned plurality of pockets is measured every palette with a reflection type photoelectric sensor. The maximum value and the minimum value of the aforementioned reflection level are obtained from data of every palette, for calculating a dispersion width defined by the difference between the maximum value and the minimum value. The aforementioned dispersion width is compared with a previously set determination threshold, for determining whether or not the dispersion width is greater than the determination threshold.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention are now described with reference to the drawings.

First Embodiment

Figure 1:
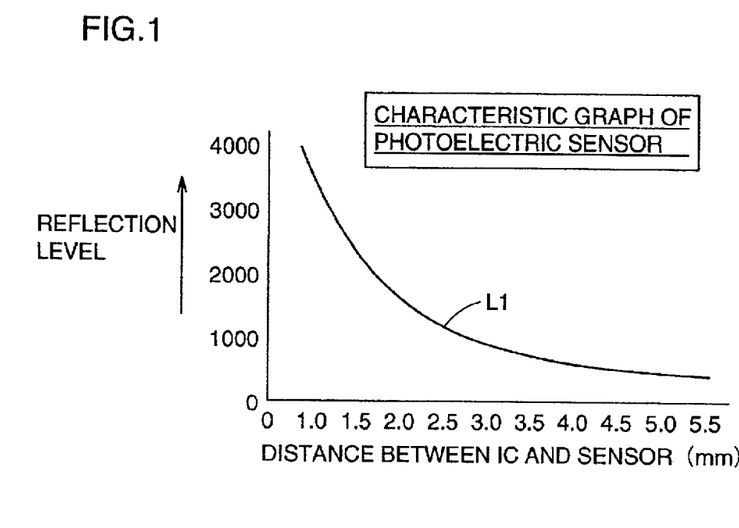
FIG. 1 is a characteristic graph of a photoelectric sensor.

FIG. 1 shows the characteristics of a reflection type photoelectric sensor employed in a first embodiment of the present invention. Referring to FIG. 1, the horizontal axis shows the distance between ICs and the reflection type photoelectric sensor, the vertical axis shows reflection levels, and a curve L1 shows characteristic change. According to the present invention, this change is remarkable and linear. The distance between the ICs and the sensor is set in the range of 1.0 mm to 2.0 mm.

Figure 2:
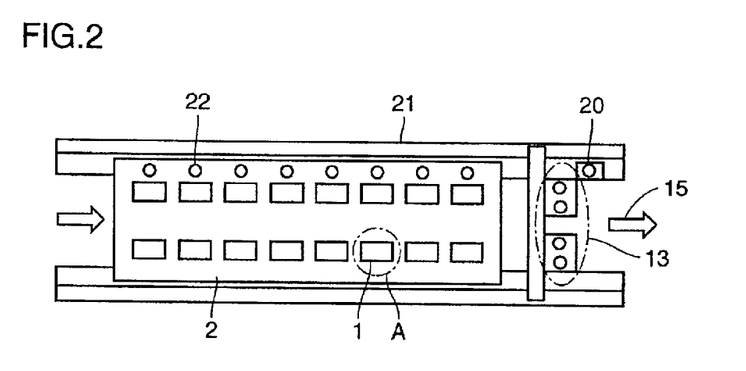
FIG. 2 is a diagram for illustrating a detection method according to a first embodiment of the present invention.
Figure 3:
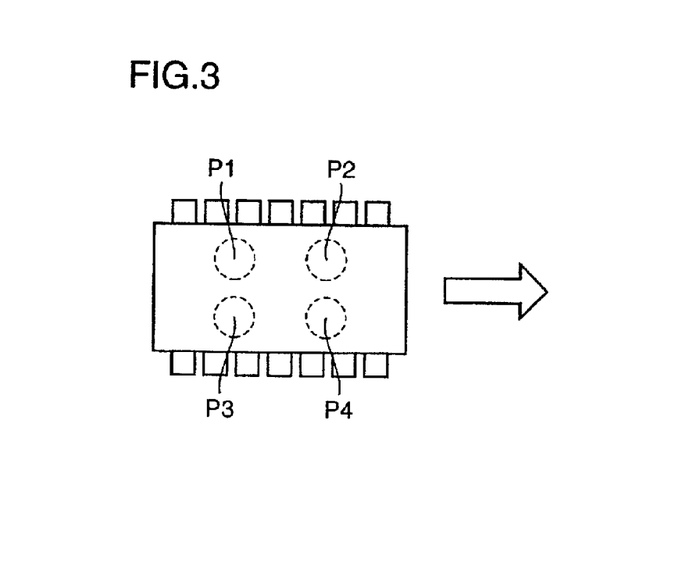
FIG. 3 is an enlarged diagram of a part A shown in FIG. 2.

FIG. 2 is a top plan view of an optical sensor type detection mechanism part according to the first embodiment. FIG. 3 is an enlarged view of a part A shown in FIG. 3.

Referring to FIG. 2, ICs 1 are stored in each of a plurality of pockets provided on the surface of a transport palette 2. The plurality of pockets are arranged in two rows on the palette 2 along the direction of transportation. The transport palette 2 is transported along arrow 15, to pass through an IC protrusion detection part 13. The transport palette 2 is transported on palette transport rails 21. Timing detection holes 22 are provided on the transport palette 2 in correspondence to a timing sensor 20.

Referring to FIG. 3, symbols P1, P2, P3 and P4 denote sampling points for sampling reflection level data. In other words, measuring points for reflection levels are arranged in two rows along the direction of transportation on each IC 1. The reflection levels of each IC 1 are measured on the two points P1 and P2 aligning with each other on one of the two rows and on the remaining two points P3 and P4 aligning with each other on the other one of the two rows.

Operations are now described. The transport palette 2 storing the ICs 1 is transferred on the transport rails 21 under a detection part having the IC protrusion detection part 13 at a constant speed rightward in FIGS. 2 and 3. The transport palette 2 has the timing detection holes 22 aligning with the respective columns of the pockets, for sampling the reflection levels on the four points P1 to P4 of each IC 1 by triggering. The reflection levels are sampled on the four points P1 to P4 for efficiently capturing slight inclination of each IC 1. The points P1 to P4 for sampling the reflection level data are set at intervals allowing detection of reflection levels of the minimum IC under the present circumstances.

Figure 4:
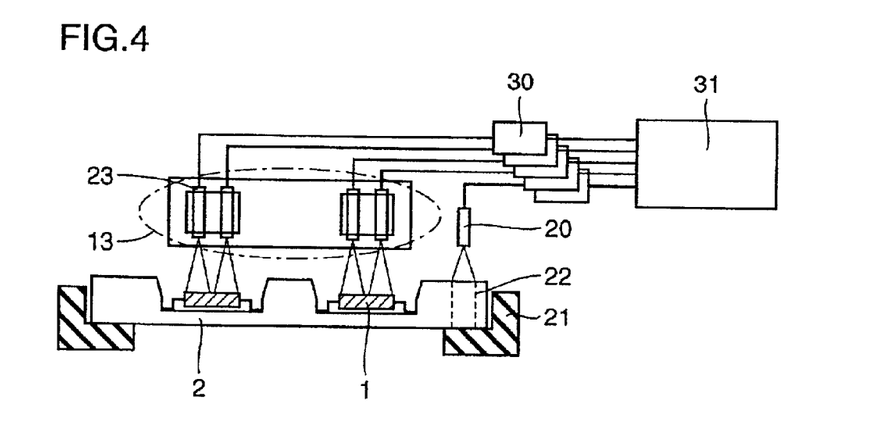
FIG. 4 is a right side elevational view of an optical sensor type detection mechanism employed in the present invention.

FIG. 4 is a detailed right side elevational view of the optical sensor type detection mechanism part shown in FIG. 2.

Referring to FIG. 4, the ICs 1 are placed on the transport palette 2. The transport palette 2 is placed on the palette transport rails 21, and transported perpendicularly to the plane of FIG. 4. The detection mechanism part comprises the IC protrusion detection part 13 and the timing sensor 20. The timing sensor 20 applies light to the timing detection holes 22 provided on the transport palette 2, thereby performing positioning. Reflection type photoelectric sensors 23 are connected to a controller 31 through sensor amplifiers 30.

The reflection type photoelectric sensors 23 arranged on the IC protrusion detection part 13 are connected to the controller 31 in one-to-one correspondence through the sensor amplifiers 30. The timing sensor 20 is also connected to the controller 31 through the corresponding sensor amplifier 30. As to a flow of signals, quantities of light received in sensor heads are A–D converted by the sensor amplifiers 30 so that digital reflection levels (0 to 4095) are written in a specific memory of the controller 31 every several msec. through cables. The controller 31 is capable of programming, and can read/write the reflection levels from/in the specific memory.

Figure 5:
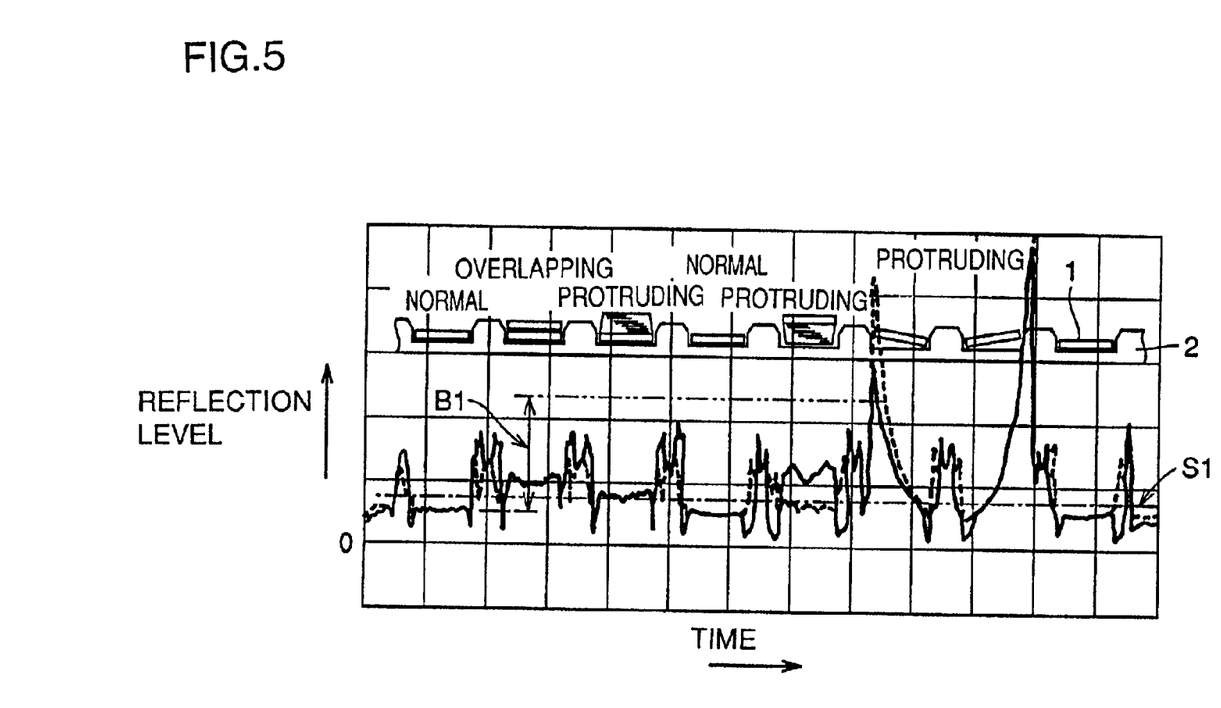
FIG. 5 illustrates a continuous waveform of reflection levels on one row captured by the optical sensor type detection mechanism part in a pseudo manner.

FIG. 5 illustrates a continuous waveform of the reflection levels on one row captured by the optical sensor type detection mechanism part shown in FIG. 4 in a pseudo manner. Black circles appearing on the waveform correspond to the reflection levels actually sampled on the points P1 to P4. Protruding ICs closer to the photoelectric sensors 23 exhibit large reflection levels. ICs 1 protruding from the corresponding pockets and approaching the photoelectric sensors 23 exhibit large reflection levels. The maximum values of the reflection levels sampled from the points P1 to P4 of the ICs 1 are obtained and stored in the memory of the controller 31. When all pockets of the transport palette 2 store the ICs 1, 8 by 2=16 reflection level data are sampled. While another type of palette receives 16 by 2=32 ICs, the palette 2 according to this embodiment receives 16 ICs 1.

The upper portion of FIG. 5 shows states of the ICs 1 stored in the pockets of the transport palette 2 in a pseudo manner. The leftmost pocket normally stores the corresponding IC 1. The second pocket stores two ICs 1 overlapping with each other in a pseudo manner. The IC 1 stored in the third pocket protrudes perpendicularly to the plane of FIG. 5 (this IC 1 is so inclined that the upper surface thereof appears in FIG. 5). The fourth pocket normally stores the corresponding IC 1. The IC 1 stored in the fifth pocket protrudes perpendicularly from the plane of FIG. 5 (this IC 1 is so inclined that the lower surface thereof appears in FIG. 5). The ICs 1 stored in the sixth and seventh pockets protrude from the pockets along the direction of transportation. The rightmost pocket normally stores the corresponding IC 1.

The algorithms of the conventional detection method (absolute value comparison) in units of ICs and the inventive detection method (dispersion determination) in units of palettes are now described.

The reflection level data of the ICs are sampled in the aforementioned manner in both methods with no difference.

In the conventional detection method (absolute value comparison) in units of ICs, the determination threshold is set between the lower limit of abnormal states and the upper limit of normal states, similarly to general determination on presence/absence of workpieces through a frequently used reflection type sensor.

This determination method is described with reference to Table 1.

TABLE 1

Exemplary Detection in Units of ICs (Absolute Value Comparison)

| Pocket Nos. 1 | Reflection Levels Sampled from ICs | | | | | Determination Formula | | |
|---|---|---|---|---|---|---|---|---|
| | P1 | P2 | P3 | P4 | Maximum Value | (Maximum Value > Threshold) | Individual Results of Determination | Total Determination |
| 2 | 1600 | 1650 | 1550 | 1620 | 1650 | 1650 > 2000 | No Abnormal Protrusion | No Abnormal Protrusion |
| 3 | 1350 | 1400 | 1450 | 1400 | 1450 | 1450 > 2000 | No Abnormal Protrusion | |
| 4 | 1700 | 1500 | 1550 | 1400 | 1700 | 1700 > 2000 | No Abnormal Protrusion | |
| 5 | 1550 | 1500 | 1550 | 1520 | 1550 | 1550 > 2000 | No Abnormal Protrusion | |
| 6 | 1500 | 1650 | 1450 | 1520 | 1650 | 1650 > 2000 | No Abnormal Protrusion | |
| ~ | Data of Nos. 7 to 11 Omitted | | | | | | No Abnormal Protrusion | |
| 12 | 1650 | 1680 | 1550 | 1620 | 1680 | 1680 > 2000 | No Abnormal Protrusion | |
| 13 | 1350 | 1400 | 1450 | 1400 | 1450 | 1450 > 2000 | No Abnormal Protrusion | |
| 14 | 1350 | 1300 | 1320 | 1200 | 1350 | 1350 > 2000 | No Abnormal Protrusion | |
| 15 | 1480 | 1450 | 1500 | 1520 | 1500 | 1500 > 2000 | No Abnormal Protrusion | |
| 16 | 1500 | 1650 | 1450 | 1500 | 1650 | 1650 > 2000 | No Abnormal Protrusion | |

Figure 6:
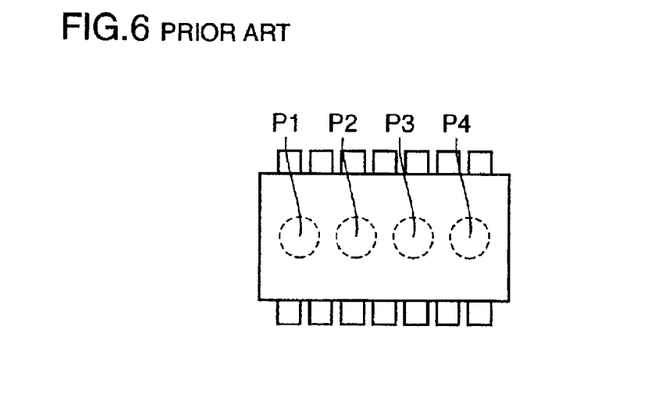
FIG. 6 illustrates sampling points $P_1$, $P_2$, $P_3$ and $P_4$ in conventional detection in units of ICs.

The optical sensor type detection mechanism part shown in FIG. 4 is employed for obtaining the maximum value of the reflection level data sampled on the points P1 to P4 shown in FIG. 6 every IC 1 and comparing the maximum value with a previously set determination threshold for determining that the IC 1 protrudes from the corresponding pocket when an inequality "maximum value>threshold" holds, i.e., when this inequality is true. The determination threshold is empirically obtained after trial and error. Referring to Table 1, all maximum values are less than the threshold, and hence the inequality is false for all ICs 1, to result in the total determination of "no abnormal protrusion".

Figure 7:
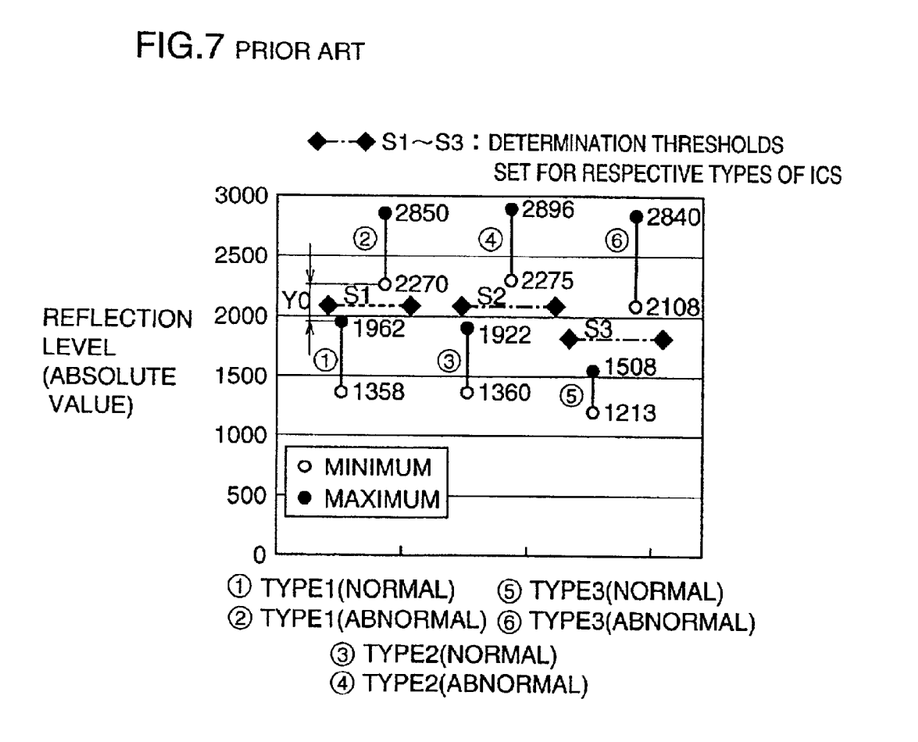
FIG. 7 illustrates distributions of reflection levels of three types of ICs sampled in normal and abnormal states in the conventional detection in units of ICs.

FIG. 7 shows distributions of reflection levels of three types of ICs sampled as to normal and abnormal states. The distributions of the ICs, all of which are plastic mold packages, are slightly different from each other. In other words, the widths between the lower limits of abnormal states and the upper limits of normal states vary with the types of the ICs. Therefore, thresholds S1 to S3 must be individually set for the respective types of ICs. As to such slight differences between the reflection levels, it has been confirmed that reflection levels are slightly vertically dispersed depending on the states of cleaning of molds in addition to the difference between molds for the respective types of ICs. When dispersion resulting from the difference between the degrees of cleaning of the molds is added to an originally small determination margin, it is difficult to make extremely stable and precise detection.

The inventive detection method (dispersion determination) in units of palettes is now described with reference to Table 2.

TABLE 2

Exemplary Dispersion Detection (Dispersion Determination)

1580 ⇩

| Pocket Nos. | Reflection Levels Sampled from ICs | | | | | In-Palette | | Determination Formula | Total Determination |
|---|---|---|---|---|---|---|---|---|---|
| | P1 | P2 | P3 | P4 | Maximum Value | Maximum Value | Minimum Value | | |
| 1 | | | | | | | | (Maximum Value− | No Abnormal |
| 2 | 1600 | 1650 | 1550 | 1620 | 1650 | | | Minimum Value > | Protrusion |
| 3 | 1350 | 1400 | 1450 | 1400 | 1450 | | | Threshold |  |
| 4 | 1700 | 1500 | 1550 | 1400 | 1700 ⟶ | 1700 | | (1700−1350) > 500 | |
| 5 | 1550 | 1500 | 1550 | 1520 | 1550 | | | When Result of the | |
| 6 | 1500 | 1650 | 1450 | 1520 | 1650 | | | above Formula is | |
| ~ | Data of Nos. 7 to 11 Omitted | | | | | | | •True: Abnormal | |
| 12 | 1650 | 1680 | 1550 | 1620 | 1680 | | | Protrusion | |
| 13 | 1350 | 1400 | 1450 | 1400 | 1450 | | | •False: No Abnormal | |
| 14 | 1350 | 1300 | 1320 | 1200 | 1350 ⟶ | | 1350 | Protrusion | |
| 15 | 1480 | 1450 | 1500 | 1520 | 1500 | | | | |
| 16 | 1500 | 1650 | 1450 | 1500 | 1650 | | | | |

⇩ Update Mean 1520

The maximum value and the minimum value are obtained from reflection level data of one palette captured by the optical sensor type detection mechanism part shown in FIG. 4, for calculating the dispersion width (MAX−MIN). This dispersion width is compared with a previously set determination *threshold, for determining that the IC protrudes from the corresponding pocket when an inequality "dispersion width>determination threshold" holds. Referring to Table 2, all dispersion widths are less than the threshold, to result in the total determination of "no abnormal protrusion".

Figure 8:
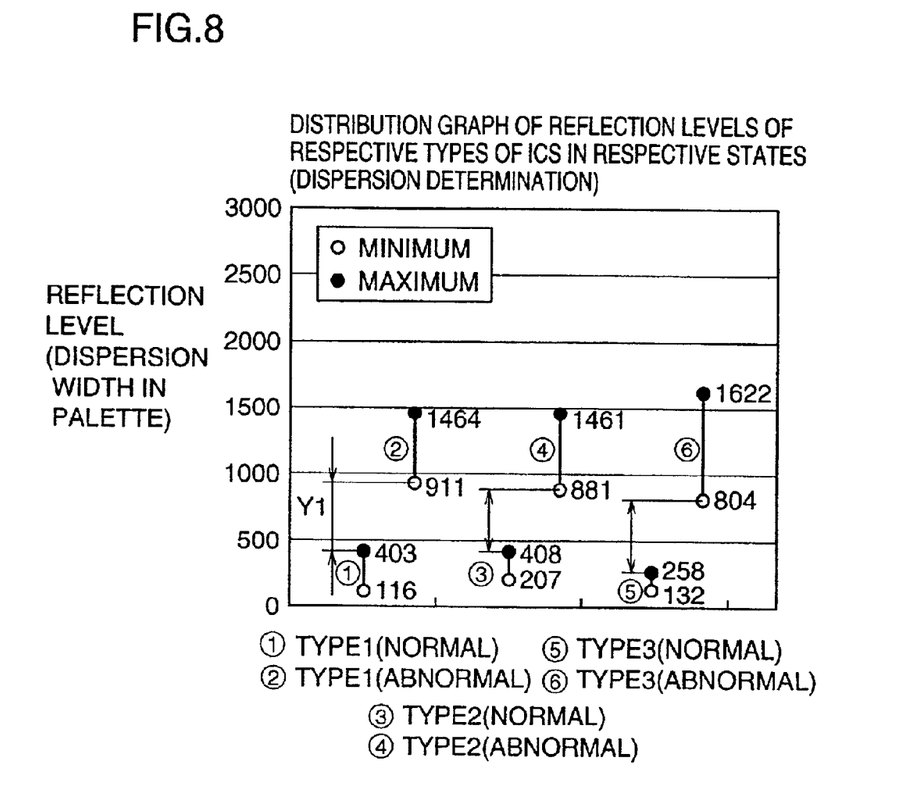
FIG. 8 illustrates distributions of reflection levels of three types of ICs (dispersion values in palettes) sampled in normal and abnormal states obtained in the present invention.

FIG. 8 shows distributions of reflection levels (dispersion values in palettes) sampled from three types of ICs in normal and abnormal states in this detection method. As compared with FIG. 7, the distributions in normal and abnormal states are substantially similar to each other regardless of the types of the ICs. In other words, the widths between the lower limits of the abnormal states and the upper limits of the normal states are constant. While reflection levels on the surfaces of molds are remarkably dispersed depending on the difference between the molds and the states of cleaning of the molds in view of the overall processing lots, while dispersion widths in normal states can be suppressed in view of small units of palettes (each storing 16 or 32 ICs) hardly influenced by the aforementioned factors. The margin $Y1$ between the upper limit of the normal states and the lower limit of the abnormal states in this method shown in FIG. 8 is about 1.65 times the margin $Y0$ in the conventional method shown in FIG. 7 in simple calculation. Thus, the margin for setting the threshold etc. can be improved for enabling highly precise detection.

While the inventive detection method (dispersion determination) in units of palettes enables highly precise detection, a fractional palette may exhibit a partially undetectable pattern. A method of solving this problem is now described.

Transport palettes, generally storing ICs in all pockets thereof, may include a fractional palette. The inventive method determines dispersion in units of palettes and hence no specific problem arises in detection when each palette stores at least two ICs. When any palette stores only one IC, however, detection cannot be performed due to absence of the object of dispersion detection. In order to solve this problem, the memory of the controller 31 stores the mean value (updated only when no protrusion is detected) of reflection levels sampled every time, for calculating the dispersion width (MAX−MIN) inclusive of the mean value for the fractional palette, thereby enabling detection also as to the fractional palette storing only one IC.

Figure 9:
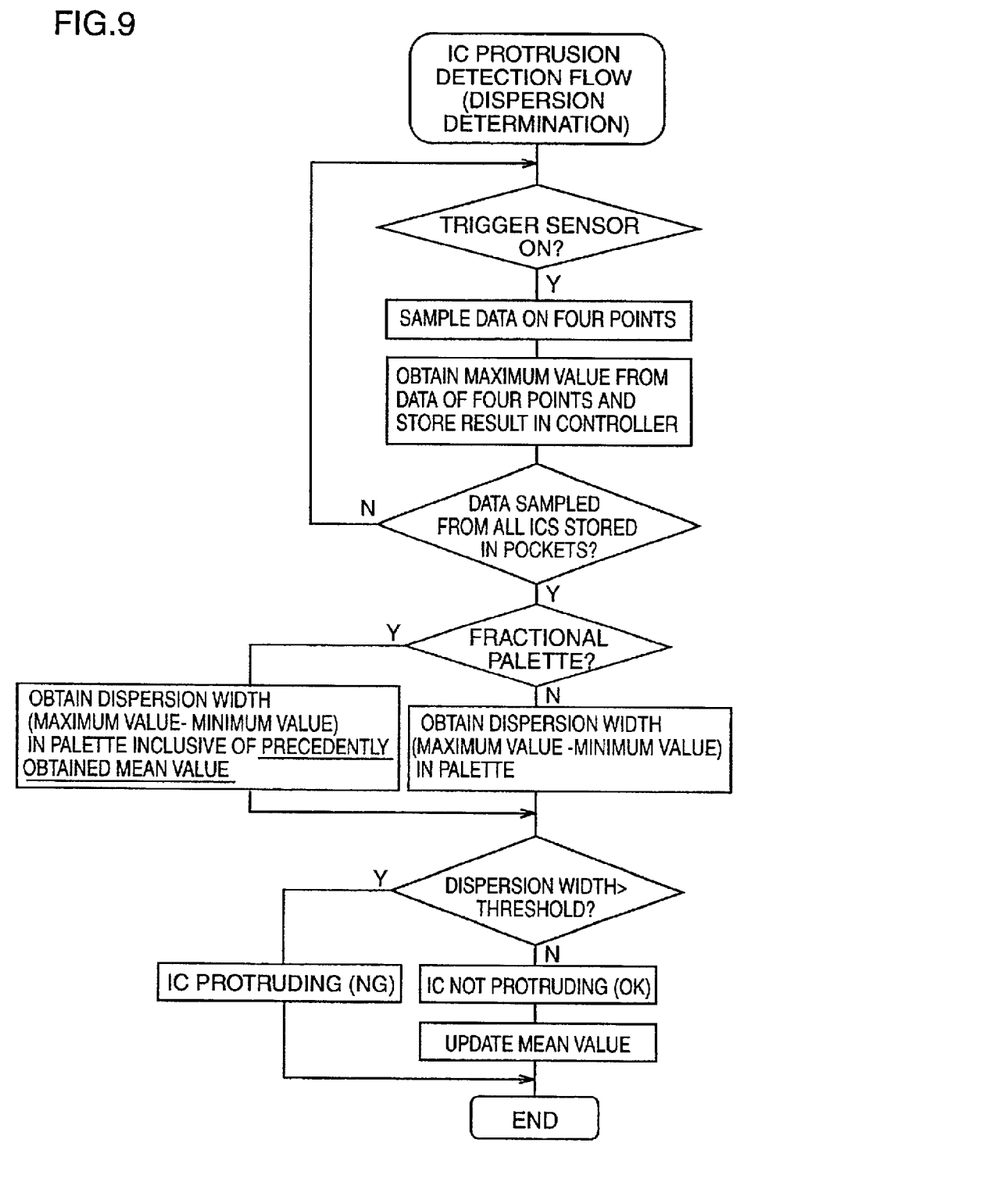
FIG. 9 is a flow chart of IC protrusion detection employing dispersion determination in units of palettes according to the present invention.

FIG. 9 is a flow chart of IC protrusion detection employing the inventive dispersion determination in units of palettes.

When such IC protrusion determination using the inventive dispersion determination in units of palettes is employed, highly precise detection is enabled for effectively reducing a socket breakage ratio and improving device workability by reducing a time for repairing sockets.

Second Embodiment

A second embodiment of the present invention relates to a method of fabricating a semiconductor device including the steps of the method of detecting protrusion of any IC from a palette described with reference to the first embodiment.

Third Embodiment

While the first embodiment of the present invention has been described with reference to the method of detecting protrusion of any IC, the present invention is not restricted to this but also applicable to an apparatus having a mechanism storing products, other than ICs, having the same shape in a dedicated palette and transporting the same. Stable product transportation can be implemented by employing an optical sensor type protrusion detection mechanism similar to the above.

According to the present invention, protrusion of an inspection object from a palette can be precisely detected for reducing a socket breakage ratio. Further, a time for repairing any socket can be reduced for effectively improving device workability.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of detecting protrusion of an inspection object from a palette, comprising steps of:

introducing an inspected object into each of a plurality of pockets provided on the surface of a palette and transporting said palette;

measuring a reflection level of said inspection object stored in each of said plurality of pockets every said palette with a reflection type photoelectric sensor;

obtaining the maximum value and the minimum value of said reflection level from data of every said palette for calculating a dispersion width defined by the difference between the maximum value and the minimum value; and comparing said dispersion width with a previously set determination threshold for determining whether or not said dispersion width is greater than said determination threshold.

2. The method of detecting protrusion of an inspection object from a palette according to claim 1, wherein said inspection object includes an IC.

3. The method of detecting protrusion of an inspection object from a palette according to claim 1, arranging measuring points for said reflection level of said inspection object in two rows along the direction of said transportation on said inspection object, for measuring said reflection level of said inspection object on two points aligning with each other on one of said two rows and two points aligning with each other on the remaining one of said two rows.

4. The method of detecting protrusion of an inspection object from a palette according to claim 1, detecting protrusion of said inspection object from corresponding said pocket as well as whether or not said inspection object overlaps with another inspection object in said corresponding pocket by said determination.

5. The method of detecting protrusion of an inspection object from a palette according to claim 1, wherein said plurality of pockets are arranged in two rows along the direction of said transportation on said palette.

6. The method of detecting protrusion of an inspection object from a palette according to claim 1, wherein the distance between said inspection object and said reflection type photoelectric sensor is set to 1.0 mm to 2.0 mm for measuring said reflection level.

7. A method of fabricating a semiconductor device comprising steps of:

introducing an IC into each of a plurality of pockets provided on the surface of a palette and transporting said palette;

measuring a reflection level of said IC stored in each of said plurality of pockets every said palette with a reflection type photoelectric sensor;

obtaining the maximum value and the minimum value of said reflection level from data of every said palette for calculating a dispersion width defined by the difference between the maximum value and the minimum value; and comparing said dispersion width with a previously set determination threshold for determining whether or not said dispersion width is greater than said determination threshold.

* * * * *